United States Patent [19]

Dage

[11] Patent Number: 4,868,182
[45] Date of Patent: Sep. 19, 1989

[54] ENHANCEMENT OF PRAZOSIN

[75] Inventor: Richard C. Dage, Cincinnati, Ohio

[73] Assignee: Merrell Dow Pharmaceuticals Inc., Cincinnati, Ohio

[21] Appl. No.: 153,542

[22] Filed: Feb. 3, 1988

Related U.S. Application Data

[63] Continuation of Ser. No. 927,785, Nov. 5, 1986, abandoned.

[51] Int. Cl.$^4$ .................. A61K 31/50; A61K 31/495; A61K 31/44; A61K 31/47; A61K 31/415
[52] U.S. Cl. .................................... 514/254; 514/300; 514/303; 514/313; 514/386
[58] Field of Search ............... 514/254, 300, 303, 313, 514/386

[56] References Cited

U.S. PATENT DOCUMENTS

| | | | |
|---|---|---|---|
| 4,130,647 | 12/1978 | Taylor | 514/254 |
| 4,578,389 | 3/1986 | Schickaender et al. | 514/254 |
| 4,584,299 | 4/1986 | Steffen et al. | 514/252 |
| 4,601,897 | 7/1986 | Saxton | 424/45 |
| 4,623,651 | 11/1986 | Grisar et al. | 514/342 |
| 4,670,450 | 6/1987 | Schenttler et al. | 514/342 |

OTHER PUBLICATIONS

J. Pharm. Pharmacol. 1980, 32(1) pp. 74–76–Dadkar et al.
European J. Pharmacology 65 (1980) 243–247–D'Armiento et al.
Handbook of Hypertension, vol. 3–Pharm. of Antihypertensive Drugs: 1984 pp. 239–248.

Primary Examiner—Douglas W. Robinson
Assistant Examiner—Raymond J. Henley, III
Attorney, Agent, or Firm—Michael J. Sayles; Stephen L. Nesbitt

[57] ABSTRACT

This invention relates to the synergistic enhancement of certain antihypertensives by the conjunctive use of certain cardiotonic agents. More specifically, this invention relates to the enhancement of the blood pressure lowering effect achieved with alpha$_1$-adrenoceptor antagonists by the conjunctive administration of cardiotonic agents possessing the ability to specifically inhibit cyclic AMP-phosphodiesterase.

8 Claims, No Drawings

ENHANCEMENT OF PRAZOSIN

CROSS-REFERENCE TO RELATED APPLICATION

This is a continuation of application Ser. No. 927,785, filed Nov. 5, 1986 and now abandoned.

This invention relates to the synergistic enhancement of certain antihypertensives by the conjunctive use of certain cardiotonic agents. More specifically, this invention relates to the enhancement of the blood pressure lowering effect achieved with alpha$_1$-adrenoceptor antagonists by the conjunctive administration of cardiotonic agents possessing the ability to specifically inhibit cyclic AMP-phosphodiesterase.

Still more specifically this invention relates to the synergistic enhancement of the antihypertensive effect of prazosin and prazosin-like compounds by the conjunctive administration of cardiotonic agents which are specific inhibitors of cardiac high affinity cyclic AMP-phosphodiesterase. These inhibitors are also known and identified as F-III PDE or Type 4 PDE inhibitors.

Prazosin, the hydrochloride salt of 1-(4-amino-6,7-dimethoxy-2-quinazolinyl-4-(2-furoyl) piperazine, is the only commercially marketed compound of its type. Its exact mechanism of action is not precisely understood, but it is well known that it is unlike conventional alpha blockers in that it causes a decrease in total peripheral resistance related to the blockade of postsynaptic alpha$_1$-adrenoceptors. Other functionally equivalent agents, e.g., trimazosin, amiquinsin, leniquinsin, quinazosin appear to possess the same type of mechanism of action as does prazosin and, as functionally equivalent alpha$_1$-adrenoceptor antagonists, are included within the scope of this application.

The cardiotonic agents which synergistically enhance the antihypertensive effect of prazosin, and other alpha$_1$-adrenoceptor blocking agents, are those compounds which normally exert their positive ionotropic effects by selective inhibition of the specific molecular form of cardiac cyclic AMP-phosphodiesterase. Generally these are identified as cardiac cyclic AMP-phosphodiesterase high affinity cyclic AMP, F-III or TYPE 4 PDE inhibitors. Further, although there is no unaminity of thought as to the specific pharmacophore required for these selective inhibitors of cardiac cyclic AMP-phosphodiesterase, such compounds generally possess (1) the presence of a strong dipole (carbonyl) at one end of the molecule, (2) an adjacent acidic proton, (3) a methyl-sized lipophilic space, (4) a relatively flat overall topography and (5) a basic or hydrogen bond acceptor site opposite the dipole. These general characteristics are associated with those cardiotonic agents possessing the ability to selectively inhibit Type 4 PDE and which are generally associated with the pharmacophores possessed by such compounds as amrinone, enoximone, 4,5-dihydro-6-[4-(1H-imidazol-1-yl)phenyl]-5-methyl-(2H)-pyridazinone, piroximone, milrinone, isomazole, OPC 8212 (Otsuka), RO-13-6438 (Roche), imazodan (Warner Lambert), ARL-57 (Tomae), Sulmazole, UD-CG-115 (Boeringer Ingleheim), UK-36,327 (Pfizer), UK-31-557, USV-2776 (U.S.V. Rohr), pimobendane and any other specific inhibitor of cyclic AMP-phosphodiesterase. This type of compound is the type of compound that selectively inhibits cyclic AMP-phosphodiesterase and as such is included within the scope of compounds which synergistically enhance the antihypertensive effect of alpha$_1$-adrenoceptor blocking agents such as prazosin and trimazosin.

In general, the specific cyclic AMP-phosphodiesterase inhibitors of this invention, (i.e., the above-described cardiotonic agents) when conjunctively administered with prazosin to effect their synergistic activity, are administered at about the threshold dose to exert a blood pressure lowering effect, i.e., the minimum dose it takes to exert a statistically significant lowering of blood pressure. This threshold dose is readily determined by standard laboratory methodology. For example, assays such as the Spontaneously Hypertensive Rat and the Anesthesized Dog for testing blood pressure effects may readily be employed to determine the threshold dose of lowering blood pressure. The threshold dose may also be approximately calculated from an in vitro IC$_{50}$ value. For this purpose the in vitro IC$_{50}$ value is the micromolar quantity of compound needed to effect a 50% inhibition of the activity of cyclic AMP-phosphodiesterase on one (1) micromolar quantity of substrate. This IC$_{50}$ value, when multiplied by the appropriate fraction for intravenous and oral administrations will yield the dosage range, in mg per kg of body weight, necessary to effect its synergism with prazosin.

On the basis of spontaneously hypertensive rat data the multiplying factor is 1/10 to 1 for the intravenous dose and 1 to 10 for the oral dose. On the basis of the anesthesized dog data the multiplying factor is 1/100 to ½ for the intravenous dose and ⅓ to 2 for the oral dose. On the basis of projected human doses the multiplying fraction is also 1/100 to ⅓ for intravenous dosing but 1/20 to ½ for oral dosing. For example, in the case of piroximone, the in vitro IC$_{50}$ value is 26 micromolar. Thus the dose range of piroximone to achieve synergism with prazosin in the SHR assay would be 2.6 to 26 mg/kg of body weight on intravenous administration and 26 to 260 mg/kg on oral administration. Analogous calculations may be made with data from dog studies and projected human doses. Results demonstrating synergy are shown in Tables 1 and 2.

Table 1 shows the synergistic results of piroximone and prazosin. In the Table, line A shows the results of the control which is the vehicle administered at an oral dose of 5 ml/kg (using 28 animals). Line B shows the results of piroximone when administered at an oral dose of 25 mg/kg (using 12 animals). Line C shows the results of prazosin when administered at an oral dose of 0.1 mg/kg (using 24 animals). Line D shows the results of the combination of piroximone (25 mg/kg) and prazosin (0.1 mg/kg) administered orally (using 24 animals).

TABLE 1

SYNERGISTIC EFFECT OF PIROXIMONE ON
PRAZOSIN IN LOWERING
BLOOD PRESSURE
IN SPONTANEOUSLY HYPERTENSIVE RATS

| | CONTROL | SYSTOLIC BLOOD PRESSURE (mmHg, x ± SE) CHANGE FROM CONTROL AT | | | |
|---|---|---|---|---|---|
| | | 1 HOUR | 2 HOURS | 3 HOURS | 4 HOURS |
| A | 222 ± 5 | −15 + 5 | −9 ± 4 | −13 ± 5 | −13 ± 4 |
| B | 228 ± 5 | −23 ± 5 | −17 ± 6 | −18 ± 7 | −20 ± 5 |
| C | 223 ± 4 | −40 ± 4+ | −40 ± 4+ | −42 ± 4+ | −35 ± 5+ |
| D | 228 ± 4 | −81 ± 5*+° | −73 ± 4*+° | −68 ± 4*+° | −63 ± 3*+° |

*Significant synergisim, $p < 0.05$
+Significant effect compound to vehicle control $p < 0.05$
°Significant difference from the effect of either agent alone Table 2 shows the synergistic results of amrinone and prazosin. In the Table, line A shows the results of the control which is the vehicle administered at an oral dose of 5 ml/kg (using 12 animals). Line B shows the results of amrinone when administered at an oral dose of 55 mg/kg (using 12 animals). Line C shows the results of prazosin when administered at an oral dose of 0.1 mg/kg (using 12 animals). Line D shows the results of the combination of amrinone (55 mg/kg) and prazosin (0.1 mg/kg) administered orally (using 12 animals).

TABLE 2

SYNERGISTIC EFFECT OF AMRINONE ON
PRAZOSIN IN LOWERING
BLOOD PRESSURE
IN SPONTANEOUSLY HYPERTENSIVE RATS

| | CONTROL | SYSTOLIC BLOOD PRESSURE (mmHg, x ± SE) CHANGE FROM CONTROL AT | | | |
|---|---|---|---|---|---|
| | | 1 HOUR | 2 HOURS | 3 HOURS | 4 HOURS |
| A | 220 ± 5 | −1 ± 8 | −4 ± 6 | −7 ± 7 | −19 ± 6 |
| B | 291 ± 7 | −26 ± 6+ | −23 ± 5+ | −21 ± 8 | −23 ± 7 |
| C | 220 ± 7 | −32 ± 3+ | −31 ± 4+ | −32 ± 4+ | −31 ± 4 |
| D | 216 ± 7 | −82 ± 8*+° | −72 ± 8*+° | −70 ± 9*+° | −58 ±*+° |

*Significant synergism, $p < 0.065$
+Significant effect compared to vehicle control, $p < 0.05$
°Significant difference from the effect of either agent alone, $p < 0.05$ It is preferable to administer the lowest amount of cyclic AMP-phosphodiesterase inhibitor in combination with the normal antihypertensive dose of prazosin. Further enhancement of the antihypertensive effect of prazosin may be achieved by increasing the amount of the inhibitor of the cyclic AMP-PDE.

In the administration of the selective Type IV PDE inhibitors to enhance the antihypertensive effect of the alpha$_1$-adrenoceptor blocking agents, it is preferred to co-administer the two agents, but the enhancement will take place so long as it is administered to the patient while the alpha$_1$-adrenoceptor blocking agent is biologically available to effect its antihypertensive action. The synergistic effect will permit a lowering of the dose of the prazosin to avoid any untoward side effects and/or will permit a more effective blood pressure lowering effect, i.e., it will help stabilize the patient to normotensive conditions. Additionally, the combination will improve cardiac function in patients with congestive heart failure, particularly those suffering with hypertension.

I claim:

1. In the treatment of hypertension with a therapeutically effective dose of an alpha$_1$-adrenoceptor antagonist selected from the group consisting of prazosin, trimazosin, amiquinsin, leniquinsin and quinazosin, the improvement which comprises the conjunctive administration of at least a threshold dose of a cardiotonic agent, capable of specifically inhibiting cardiac high affinity cyclic AMP-phosphodiesterase, selected from the group consisting of imadazon enoximone, piroximone, amrinone, milrinone, isomazole, pimobendane, and 4,5-dihydro-6-[4-(1H-imidazol-1-yl)-phenyl]-5-methyl-2H-pyridazinone.

2. A method of claim 1 wherein the alpha$_1$-adrenoceptor antagonist is prazosin.

3. A method of claim 2 wherein the cardiotonic agent is enoximone.

4. A method of claim 2 wherein the cardiotonic agent is amrinone.

5. A method of claim 2 wherein the cardiotonic agent is 4,5-dihydro-6-[4-(1H-imidazol-1-yl)phenyl]-5-methyl-(2H)-pyridazinone.

6. A method of claim 2 wherein the cardiotonic agent is piroximone.

7. A method of claim 2 wherein the cardiotonic agent is imadazon.

8. A method of claim 2 wherein the cardiotonic agent is isomazole.

* * * * *